(12) United States Patent
Choi et al.

(10) Patent No.: US 9,006,135 B2
(45) Date of Patent: Apr. 14, 2015

(54) ABSORBENT COMPRISING HYDROPHOBIC MESOPOROUS MATERIAL FOR REMOVAL OF HARMFUL PHARMACEUTICALS FROM AQUEOUS ENVIRONMENT

(75) Inventors: Heechul Choi, Gwangju (KR); Tung Xuan Bui, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 636 days.

(21) Appl. No.: 13/325,529

(22) Filed: Dec. 14, 2011

(65) Prior Publication Data

US 2012/0172213 A1 Jul. 5, 2012

(30) Foreign Application Priority Data

Jan. 5, 2011 (KR) .................. 10-2011-0001112

(51) Int. Cl.
*B01J 20/20* (2006.01)
*B01J 20/10* (2006.01)
*B01J 20/22* (2006.01)
*B01J 20/28* (2006.01)
*B01J 20/30* (2006.01)
*C02F 1/28* (2006.01)
*C07F 7/18* (2006.01)
*C02F 101/32* (2006.01)

(52) U.S. Cl.
CPC .............. *B01J 20/103* (2013.01); *B01J 20/223* (2013.01); *B01J 20/28064* (2013.01); *B01J 20/28073* (2013.01); *B01J 20/28083* (2013.01); *B01J 20/3085* (2013.01); *C02F 1/281* (2013.01); *C02F 2101/32* (2013.01); *C07B 2200/00* (2013.01); *C07F 7/1844* (2013.01)

(58) Field of Classification Search
CPC .... B01J 20/103; B01J 20/223; B01J 20/3085; B01J 20/28064; B01J 20/28073; B01J 20/28083; C02F 1/28; C07F 7/1844
USPC .................. 502/400, 401, 407; 423/335–340
See application file for complete search history.

(56) References Cited

PUBLICATIONS

Bui et al., "Organically functionalized mesoporous SBA-15 as sorbents for removal of selected pharmaceuticals from water," Journal of Hazardous Materials 193 (2011)156-163: Published online Jul. 20, 2011.*
Bui, Tung Xuan and Heechul Choi, "Adsorptive removal of selected pharmaceuticals by mesoporous silica SBA-15," Journal of Hazardous Materials 168 (2009)602-608, Published online Feb. 22, 2009.*
Wang et al., "H NMR Studies of Simple Organic Groups Covalently Attached to Ordered Mesoporous Silica," J. Phys. Chem. C 2009, 113, 18142-18151: Published Online Sep. 28, 2009.*
Zhao et al., "Triblock Copolymer Syntheses of Mesoporous Silica with Periodic 50 to 300 Angstrom Pores," Science vol. 279, Jan. 23, 1998, p. 548-.*

(Continued)

*Primary Examiner* — Anthony J Zimmer
(74) *Attorney, Agent, or Firm* — Nath, Goldberg & Meyer; Joshua B. Goldberg; Katelyn J. Bernier

(57) ABSTRACT

This invention relates to an absorbent including trimethylsilylated mesoporous silica SBA-15, and more particularly to an absorbent including trimethylsilylated mesoporous silica SBA-15, which can effectively remove 90% or more of the seven pharmaceuticals of carbamazepine, diclofenac, estrone, gemfibrozil, ibuprofen, ketoprofen, and trimethoprim which are present in high concentration.

7 Claims, 2 Drawing Sheets

(56) References Cited

PUBLICATIONS

Kisler et al. "Adsorption of Proteins on Mesoporous Molecular Sieves". Materials Physics and Mechanics. 2001, 4, pp. 89-93.

Kubota et al. "Further Investigations on the Promoting Effect of Mesoporous Silica on Base-Catalyzed Aldol Reaction". Topics in Catalysis. 2010, 53, pp. 492-499.

* cited by examiner

ABSORBENT COMPRISING HYDROPHOBIC MESOPOROUS MATERIAL FOR REMOVAL OF HARMFUL PHARMACEUTICALS FROM AQUEOUS ENVIRONMENT

CROSS-REFERENCE TO RELATED APPLICATION

This application claims the benefit under 35 U.S.C. §119 of Korean Patent Application No. 10-2011-0001112, filed on Jan. 5, 2011 in the Korean Intellectual Property Office, the entirety of which is incorporated herein by reference.

BACKGROUND OF THE INVENTION

1. Technical Field

The present invention relates to an absorbent for organic pharmaceuticals, comprising a hydrophobic mesoporous material, and more particularly to an absorbent for organic pharmaceuticals, which comprises a hydrophobic mesoporous material that is very efficient at removing harmful pharmaceuticals which are micropollutants from an aqueous environment.

2. Description of the Related Art

In the past few years, a number of reports have been made of research results about using mesoporous silica for the delivery of pharmaceuticals. Since the first report of mesoporous silica having an ordered pore array in 1992, thorough research into the synthesis, analysis and applications thereof has been ongoing. Nanoparticles, which have an ordered pore array structure and a large surface area and pore volume, are widely used in the bio field including delivery of pharmaceuticals, enzymes, DNAs, etc., and nanoparticles applicable to the bio field are being used for diagnosis, imaging, treatment or the like. In particular, mesoporous silica is suitable for use as a medium for the delivery of pharmaceuticals because it is not toxic and has an appropriate pore size, a large surface area, and sufficient Si—OH bonds on the surface of pores. Compared to typical mesoporous silica shells, the use of hollow mesoporous silica cores and mesoporous shells is more proper for the delivery of pharmaceuticals. Furthermore, they exhibit superior release of pharmaceuticals and may be ingested or injected and are thus widely used to deliver pharmaceuticals. Hence, mesoporous silica nanoparticles are utilized as a multifunctional structure responsible for light emission, magnetic force, display of cells, therapeutic functions, etc.

Also, mesoporous silica may be used as an insulating film for semiconductors composed of an organic-inorganic composite wherein mesoporous silica having a pore size of 2~50 nm, and preferably 2~10 nm is dispersed in an organic polymer.

Because of the above-mentioned properties, mesoporous silica is recently receiving attention as an absorbent for removing micropollutants such as harmful pharmaceuticals, which is regarded as an environmental issue. Typically, pharmaceuticals are released into the environment directly or indirectly via sewage disposal plants. This is because sewage disposal plants which are currently being used cannot completely remove pharmaceuticals. The pharmaceuticals are present up to 10 µg/L$^{-1}$ in an aqueous environment, and also in special cases (e.g. upon discharge of sewage from pharmaceutical manufacturers or plants), pharmaceuticals at 100 µg/L$^{-1}$ are found. In the aqueous environment, the residue of pharmaceuticals may be toxic to microorganisms including human beings, fish, and aquatic organisms. Furthermore, antibiotic pharmaceuticals may form a tolerance to antibiotics or more severe phenomena. Accordingly, activated carbon is effectively used as an absorbent for removing many pharmaceuticals. However, the efficient removal of such pharmaceuticals is in need of the selective use of absorbents.

Among mesoporous silica species, SBA-15 was first synthesized in 1998, and two kinds of synthesis methods are mainly applied because they are very simple and easily reproducible. Although SBA-15 having a large pore size (~8 nm) serves as a template for synthesizing a catalyst or absorbent, SBA-15 itself does not exhibit high activity as an absorbent for removing pollutants, in particular, organic pollutants.

Therefore, there is the continuous need to develop the mesoporous silica that hereto has been used in a variety of fields, so that it may be used in various applications that can utilize the properties thereof.

SUMMARY OF THE INVENTION

Accordingly, the present invention has been made keeping in mind the problems encountered in the related art and the present invention is intended to provide an absorbent which is useful in removing harmful pharmaceuticals by modifying the surface of mesoporous silica, in particular, SBA-15.

To this end, the present invention provides an absorbent for organic pharmaceuticals, comprising trimethylsilylated SBA-15.

According to an embodiment of the present invention, the trimethylsilylated SBA-15 may have an ordered structure, with a surface area of 500~600 m$^2$/g, a pore volume of 0.7~0.9 cm$^3$/g, and a pore size of 6~8 nm.

According to an embodiment of the present invention, the trimethylsilylated SBA-15, which is hydrophobic via trimethylsilylation of SBA-15 and thus exhibits high activity for organic pollutants, may remove harmful organic pharmaceuticals.

According to another embodiment of the present invention, a method of preparing trimethylsilylated SBA-15 is provided, which comprises (1) preparing a mixture solution of Pluronic® P-123 and tetraethylorthosilicate in an acid solution, (2) allowing the mixture solution to stand at 25~40° C. for 10~30 hours and performing stirring at 80~120° C. for 20~30 hours, (3) washing the mixture solution obtained in (2) with deionized water and performing calcination at 400~600° C. for 4~8 hours, thus obtaining SBA-15, (4) pretreating the SBA-15 at 170~210° C. for 10~14 hours in a vacuum, (5) creating a slurry of the pretreated SBA-15 and anhydrous toluene over a period of time ranging from 20 min to 1 hour, and (6) adding the slurry with hexamethyldisilazane in a nitrogen atmosphere and performing stirring at 25~30° C. for 20~30 hours, thus obtaining trimethylsilylated SBA-15, which is then filtered.

Also, the method of preparing trimethylsilylated SBA-15 may further comprise (7) continuously washing the trimethylsilylated SBA-15 with toluene, ethanol and acetone and performing drying at 80~120° C. for 10~15 hours in a vacuum.

According to a preferred embodiment of the present invention, the trimethylsilylated SBA-15 may remove 90% or more of carbamazepine, diclofenac, estrone, gemfibrozil, ibuprofen, ketoprofen, and trimethoprim from an aqueous phase, pH 5.6.

BRIEF DESCRIPTION OF THE DRAWINGS

The features and advantages of the present invention will be more clearly understood from the following detailed description taken in conjunction with the accompanying drawings, in which.

DESCRIPTION OF SPECIFIC EMBODIMENTS

Figure 1:
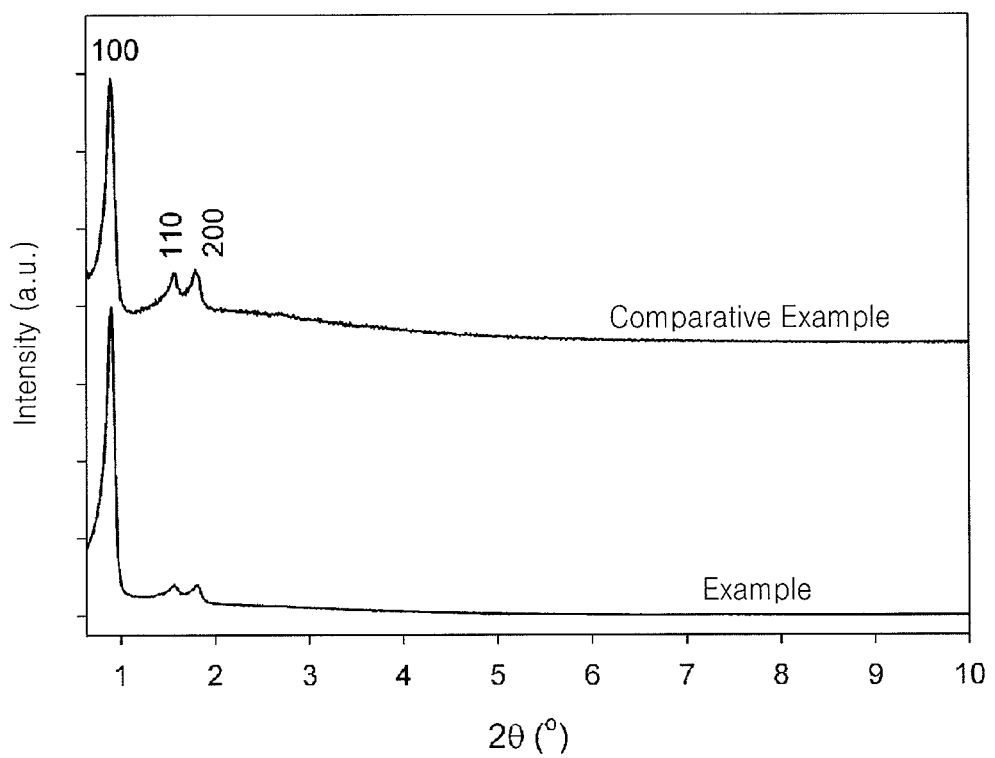
FIG. 1 is a graph showing X-ray diffraction patterns of the comparative example and the example.

According to the present invention, an absorbent for organic pharmaceuticals comprises mesoporous silica SBA-15 is trimethylsilylated and thus becomes hydrophobic, thereby exhibiting a high ability to remove harmful pharmaceuticals.

The absorbent for organic pharmaceuticals according to the present invention comprises trimethylsilylated SBA-15.

Trimethylsilylated SBA-15 is a known material, and in the present invention has a surface area of 500~600 m$^2$/g, a pore volume of 0.7~0.9 cm$^3$/g, and a pore size of 6~8 nm. If the surface area, pore volume and pore size of this silica fall outside the above ranges, it is undesirably difficult to efficiently remove the pharmaceuticals.

The trimethylsilylated SBA-15 is a kind of mesoporous material, wherein SBA is an abbreviated form of Santa Barbara. The trimethylsilylated SBA-15 is in the form of one-dimensional nanopores in a regular hexagonal arrangement, and may be prepared in an acidic atmosphere (pH 1~2), and manifests superior hydrothermal stability.

In the present invention, trimethylsilylated SBA-15 has an ability to remove harmful organic pharmaceuticals, by trimethylsilylating SBA-15 which does not show high activity for organic pollutants so that it becomes hydrophobic thus exhibiting high activity for organic pollutants.

The trimethylsilylated SBA-15 may be synthesized using known methods. For example, a method of synthesizing mesoporous silica SBA-15 is disclosed in Science, 1998, 279, 548-552, Zhao, D., but is not limited thereto, and SBA-15 may be prepared using the above method, followed by performing a post-grafting process, thus obtaining trimethylsilylated SBA-15.

According to the present invention, a method of preparing the trimethylsilylated SBA-15 includes (1) preparing a mixture solution of Pluronic® P-123 and tetraethylorthosilicate in an acidic solution, (2) allowing the mixture solution to stand at 25~40° C. for 10~30 hours and performing stirring at 80~120° C. for 20~30 hours, (3) washing the mixture solution obtained in (2) with deionized water and performing calcination at 400~600° C. for 4~8 hours, thus obtaining SBA-15, (4) pretreating the SBA-15 at 170~210° C. for 10~14 hours in a vacuum, (5) creating a slurry of the pretreated SBA-15 and anhydrous toluene over a period of time ranging from 20 min to 1 hour, and (6) adding the slurry with hexamethyldisilazane in a nitrogen atmosphere and performing stirring at 25~30° C. for 20~30 hours, thus obtaining trimethylsilylated SBA-15, which is then filtered.

Also, the method of preparing the trimethylsilylated SBA-15 further includes (7) continuously washing the trimethylsilylated SBA-15 with toluene, ethanol and acetone and performing drying at 80~120° C. for 10~15 hours in a vacuum.

Specifically in (1), Pluronic® P-123 is mixed with tetraethylorthosilicate in an acidic solution, and the mixing ratio of Pluronic® P-123 and tetraethylorthosilicate is not particularly limited but may be for example 1:9~9:1.

As such, Pluronic® P-123 has a nominal chemical formula of HO(CH$_2$CH$_2$O)$_{20}$(CH$_2$CH(CH$_3$)O)$_{70}$(CH$_2$CH$_2$O)$_{20}$H, with a molecular weight of about 5800 Da, and may also be identified as poly(ethylene glycol)-block-poly(propylene glycol)-block-poly(ethylene glycol) or PEG-PPG-PEG.

The acidic solution may be selected from among hydrochloric acid, sulfuric acid, and nitric acid.

In (2), the mixture solution may be allowed to stand at 25~40° C. for 10~30 hours and stirred at 80~120° C. for 20~30 hours. If this procedure is carried out outside the above ranges, the specific surface area and the pore size may undesirably become smaller.

In (3), the mixture solution obtained in (2) may be washed with deionized water and calcined at 400~600° C. for 4~8 hours thus obtaining SBA-15. If this procedure is conducted outside the above ranges, the organic material used as a template may not be completely removed.

In (4) and (5), the SBA-15 may be pretreated at 170~210° C. for 10~14 hours in a vacuum, and turned into a slurry by mixing with anhydrous toluene over a period of time ranging from 20 min to 1 hour. If these procedures are conducted outside the above ranges, moisture may be left behind, and thus surface modification does not efficiently take place.

In (6), the slurry may be added with hexamethyldisilazane in a nitrogen atmosphere and stirred at 25~30° C. for 20~30 hours, thus obtaining trimethylsilylated SBA-15 which is then filtered. If this procedure is conducted outside the above ranges, SBA-15 may not be well trimethylsilylated, and complete surface modification may not take place undesirably.

In (7), the trimethylsilylated SBA-15 may be continuously washed with toluene, ethanol, and acetone and dried at 80~120° C. for 10~15 hours in a vacuum. If this procedure is conducted outside the above ranges, the hexamethyldisilazane, toluene, ethanol, and acetone may not be completely removed.

The amount of hexamethyldisilazane may be 0.01~10 parts by weight based on 100 parts by weight of SBA-15. If the amount thereof is less than 0.01 parts by weight, surface modification may not completely occur. In contrast, if the amount thereof exceeds 10 parts by weight, economic loss may be caused due to excessive use of hexamethyldisilazane.

The absorbent for organic pharmaceuticals according to the present invention is capable of removing carbamazepine, diclofenac, estrone, gemfibrozil, ibuprofen, ketoprofen, and trimethoprim from an aqueous phase.

The rate of removing carbamazepine, diclofenac, estrone, gemfibrozil, ibuprofen, ketoprofen, and trimethoprim by the absorbent for organic pharmaceuticals according to the present invention may be 90% or more.

The following examples are set forth to illustrate the present invention and are not to be construed as limiting it, and may provide a better understanding of the present invention.

Comparative Example and Example

Comparative Example 1

8 g of Pluronic® P-123, 240 g of 2M hydrochloric acid solution, and 6.4 ml of tetraethylorthosilicate were mixed with 60 g of deionized water, thus preparing a mixture.

This mixture was stirred at 35° C. for 24 hours, further stirred at 100° C. for 24 hours, washed with deionized water, and calcined at 500° C. for 6 hours, thus obtaining SBA-15.

Example 1

Trimethylsilylated SBA-15 was prepared using post-grafting.

SBA-15 (0.4 g) obtained in Comparative Example 1 was pretreated at 190° C. for 12 hours in a vacuum, and turned into a slurry by mixing with anhydrous toluene (100 ml) for 30 min. Subsequently, hexamethyldisilazane (2.36 ml) was added in a nitrogen atmosphere, and the resulting mixture was then stirred at 25° C. for 24 hours, thus obtaining trimethylsilylated SBA-15. This trimethylsilylated SBA-15 was filtered, continuously washed with toluene, ethanol and acetone, and finally dried at 100° C. for 12 hours in a vacuum, and stored in a desiccator.

The materials obtained in Comparative Example 1 and Example 1 were measured using X-ray diffraction (XRD), $N_2$ adsorption-desorption, FTIR spectroscopy, and elemental analysis.

With reference to FIG. 1, the XRD patterns of the materials of Comparative Example 1 and Example 1 showed three well-resolved peaks, which indexed as (100), (110), (200) in the hexagonal P6mm symmetry. This means that inactivity was maintained while the mesostructure of SBA-15 was functionalized. However, a small decrease in spacing value ($a_0$) was observed in Example 1 ($a_0$=11.2 nm) compared to Comparative Example 1 ($a_0$=11.4 nm), which indicates changes in wall thickness and pore size because of the desorption of organosilane.

Using nitrogen adsorption-desorption, the specific surface area, pore volume and pore diameter of the materials of Comparative Example 1 and Example 1 were measured. The material of Comparative Example 1 had a BET surface area of 837 $m^2/g$, a pore volume of 1.04 $cm^3/g$, a pore diameter of 7.2 nm, and a wall thickness of 4.2 nm, and the material of Example 1 had a BET surface area of 565 $m^2/g$, a pore volume of 0.75 $cm^3/g$, a pore diameter of 6.7 nm, and a wall thickness of 4.5 nm.

Thus, the introduction of a trimethylsilyl functional group increased the thickness of the wall of mesoporous silica while decreasing the specific surface area, pore volume, and pore diameter thereof.

The presence of the functional group in the materials of Comparative Example 1 and Example 1 were confirmed by FTIR spectra.

Figure 2:
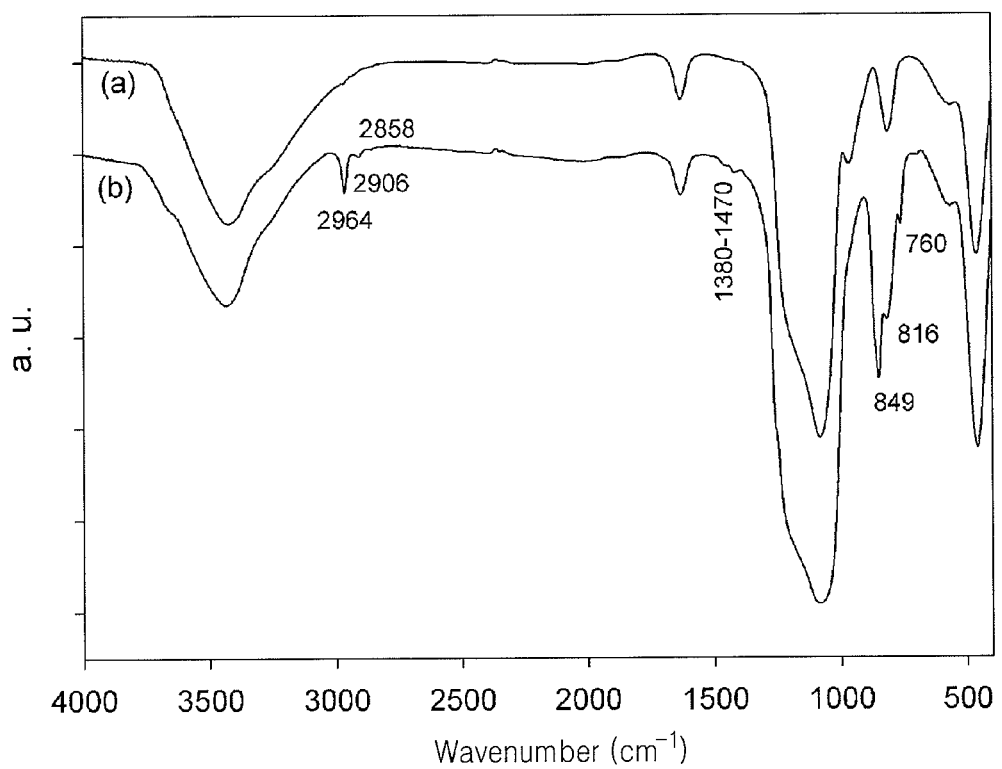
FIG. 2 is a graph showing FTIR (Fourier Transform Infra-Red) spectra of the comparative example and the example.

FIG. 2 shows FTIR spectra of the synthesized materials. In Comparative Example 1, the presence of a typical So—O—Si band was confirmed by the peaks at about 1080~1200, 806, and 458 $cm^{-1}$ associated with the formation of concentrated silica network. The weak peak associated with the Si—O stretching mode of the isolated Si—OH group at about 965 $cm^{-1}$ was also present in Comparative Example 1. This band was observed in Example 1, and the SiOH group appeared to be used for functionalization. The bands at 1460, 2800~3000 $cm^{-1}$ associated with aliphatic C—H vibration were observed in the spectrum of the comparative example. The sharp peak at 2964 $cm^{-1}$ and two weak adsorption bands at 2906 and 2858 $cm^{-1}$ were measured as the symmetric C—H stretching modes of a methyl group. The adsorption band in the range of 1380~1470 $cm^{-1}$ is associated with symmetric and asymmetric C—H bending modes of the methyl group. Also, the sharp adsorption band at 849 $cm^{-1}$ and two small shoulder peaks at 816 and 760 $cm^{-1}$ were measured as Si—C stretching modes.

Thus, the presence of the trimethylsilyl group in Example 1 was apparently demonstrated by FTIR.

Elemental analysis revealed that the amount of the functional group of Example 1 was 1.60 mol $Si(CH_3)_3$ group/g (or 1.91 μmol/$m^2$, 1.15 group/$nm^2$). The element of nitrogen was not detected from the sample, which means that a byproduct, $NH_3$, was completely washed off.

<Measurement of Adsorption of Pharmaceuticals>

With reference to Table 1, the material of Example 1 can be seen to have a high ability to effectively adsorb seven different pharmaceuticals which are present in high concentration.

The seven pharmaceuticals of carbamazepine, diclofenac, estrone, gemfibrozil, ibuprofen, ketoprofen, and trimethoprim as shown in Table 1 were batch tested using the materials of Example 1 and Comparative Example 1. In respective tests, the adsorbed amount was 1 g/L, and the initial concentration of each pharmaceutical was 100 μg/L. The pH of the solution was maintained at 5.6 and 7.0 using a buffer, and a constant ionic strength of 10 mM was maintained with NaCl. The test was conducted after incubation at 25° C. and 200 rpm for 24 hours. After the test, the sample was filtered, extracted using solid phase extraction, and analyzed using LC-tandem MS.

TABLE 1

| Absorbent | pH | Carbamazepine | Diclofenac | Estrone | Gemfibrozil | Ibuprofen | Ketoprofen | Trimethoprim (unit: %) |
|---|---|---|---|---|---|---|---|---|
| C. Ex. 1 | 7.0 | 11.8 | 4.0 | 0.0 | 13.7 | 0.0 | 1.7 | 36.9 |
|  | 5.6 | 30.3 | 4.1 | 28.5 | 45.8 | 4.0 | 8.6 | 60.6 |
| Ex. 1 | 7.0 | 85.1 | 27.5 | 69.0 | 99.0 | 52.5 | 19.3 | 97.5 |
|  | 5.6 | 93.2 | 94.8 | 99.4 | 100.0 | 95.3 | 90.5 | 94.7 |

These values are average values obtained by repeating the same test several times.

As is apparent from Table 1, the material of Comparative Example 1 could limitedly adsorb only 11~40% of carbamazepine, gemfibrozil, and trimethoprim at pH 7.0, and the other pharmaceuticals were slightly adsorbed.

In the case of Comparative Example 1, when the pH was decreased to 5.6, the adsorption of the above-mentioned three pharmaceuticals and estrone was gradually increased, but the adsorption results were 60% or less.

The material of Example 1 adsorbed, at pH 7.0, 69.0% of estrone, 85.1% of carbamazepine, 99.0% of gemfibrozil, and 97.5% of trimethoprim, and also exhibited slightly low adsorptions, including 27.5% of dichlofenac, 52.5% of ibutrofen, and 19.3% of ketoprofen, but these were higher compared to when using the material of Comparative Example 1. At pH 5.6, the material of Example 1 had adsorption effects of 90% or more of all the pharmaceuticals. In particular, 100% of the gemfibrozil was removed.

Thus, the absorbent comprising the trimethylsilylated SBA-15 according to the present invention can effectively remove the seven pharmaceuticals of carbamazepine, diclofenac, estrone, gemfibrozil, ibuprofen, ketoprofen, and trimethoprim from an aqueous phase, thus exhibiting high adsorption rate.

As described hereinbefore, the present invention provides an absorbent comprising a hydrophobic mesoporous material for removing harmful pharmaceuticals from an aqueous environment. In the absorbent for organic pharmaceuticals according to the present invention, mesoporous silica, SBA-15, can be chemically bound with a variety of functional groups via reaction with organosilane and thus becomes hydrophobic, thus exhibiting a very high ability to adsorb organic pollutants and thereby removing harmful pharmaceuticals. Particularly the absorbent according to the present invention can effectively remove 90% or more of the seven pharmaceuticals carbamazepine, diclofenac, estrone, gemfibrozil, ibuprofen, ketoprofen, and trimethoprim, which are present in high concentration.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An absorbent for organic pharmaceuticals comprising: trimethylsilylated SBA-15 having a surface area of 500-600 $m^2/g$, a pore volume of 0.7-0.9 $cm^3/g$, and a pore size of 6-8 nm.

2. A method of preparing trimethylsilylated SBA-15 comprising:
   (1) preparing a mixture solution of PEG-PPG-PEG and tetraethylorthosilicate in an acid solution;
   (2) allowing the mixture solution to stand at 25-40° C. for 10-30 hours and performing stirring at 80-120° C. for 20-30 hours;
   (3) washing the mixture solution obtained in (2) with deionized water and performing calcination at 400-600° C. for 4-8 hours, thus obtaining SBA-15;
   (4) pretreating the SBA-15 at 170-210° C. for 10-14 hours in a vacuum;
   (5) creating a slurry of the pretreated SBA-15 and anhydrous toluene over a period of time ranging from 20 min to 1 hour; and
   (6) adding the slurry with hexamethyldisilazane in a nitrogen atmosphere and performing stirring at 25-30° C. for 20-30 hours, thus obtaining trimethylsilylated SBA-15, which is then filtered.

3. The method of claim 2, further comprising (7) continuously washing the trimethylsilylated SBA-15 with toluene, ethanol and acetone and performing drying at 80-120° C. for 10-15 hours in a vacuum.

4. The method of claim 2, wherein the trimethylsilylated SBA-15 removes 90% or more of carbamazepine, diclofenac, estrone, gemfibrozil, ibuprofen, ketoprofen, and trimethoprim from an aqueous phase at pH 5.6.

5. The method of claim 2, wherein an amount of the hexamethyldisilazane is 0.01-10 parts by weight based on 100 parts by weight of SBA-15.

6. Trimethylsilylated SBA-15 having a surface area of 500-600 $m^2/g$, a pore volume of 0.7-0.9 $cm^3/g$, and a pore size of 6-8 nm, prepared using a preparation method comprising (1) preparing a mixture solution of PEG-PPG-PEG and tetraethylorthosilicate in an acid solution; (2) allowing the mixture solution to stand at 25-40° C. for 10-30 hours and performing stirring at 80-120° C. for 20-30 hours; (3) washing the mixture solution obtained in (2) with deionized water and performing calcination at 400-600° C. for 4-8 hours, thus obtaining SBA-15; (4) pretreating the SBA-15 at 170-210° C. for 10-14 hours in a vacuum; (5) creating a slurry of the pretreated SBA-15 and anhydrous toluene over a period of time ranging from 20 min to 1 hour; and (6) adding the slurry with hexamethyldisilazane in a nitrogen atmosphere and performing stirring at 25-30° C. for 20-30 hours, thus obtaining trimethylsilylated SBA-15, which is then filtered.

7. The trimethylsilylated SBA-15 of claim 6, which is prepared using the preparation method further comprising (7) continuously washing the trimethylsilylated SBA-15 with toluene, ethanol and acetone and performing drying at 80-120° C. for 10-15 hours in a vacuum.

* * * * *